United States Patent [19]

Tanaka

[11] Patent Number: 4,502,784
[45] Date of Patent: Mar. 5, 1985

[54] ANALYZER COMPENSATION CIRCUIT

[75] Inventor: Masaru Tanaka, Kyoto, Japan

[73] Assignee: Horiba, Ltd., Kyoto, Japan

[21] Appl. No.: 401,270

[22] Filed: Jul. 23, 1982

[30] Foreign Application Priority Data

Sep. 17, 1981 [JP] Japan ............... 56-148413

[51] Int. Cl.³ .................. G01J 1/18; G01N 21/17
[52] U.S. Cl. .................. 356/222; 356/229; 356/319; 356/435; 377/53
[58] Field of Search ............ 356/435, 229, 222, 448, 356/72, 319, 320, 323, 325; 250/435, 209, 214 RC, 565; 328/208, 211; 377/53

[56] References Cited

U.S. PATENT DOCUMENTS

| 2,803,752 | 8/1957 | Warren | 356/435 X |
| 2,939,361 | 6/1960 | Hock | 356/435 |
| 3,272,969 | 9/1966 | Cutaia | 377/53 X |
| 3,522,739 | 8/1970 | Coor et al. | 356/320 |
| 3,528,749 | 9/1970 | Bowker | 356/222 X |
| 3,738,756 | 6/1973 | Chaney | 356/368 |
| 3,879,135 | 4/1975 | Egli et al. | 356/435 |
| 3,986,776 | 10/1976 | George | 356/323 X |
| 4,080,075 | 3/1978 | Berg | 356/435 X |
| 4,320,970 | 3/1982 | Dowben et al. | 356/317 |
| 4,350,441 | 9/1982 | Wicnienski | 250/565 X |

Primary Examiner—Vincent P. McGraw
Assistant Examiner—S. A. Turner
Attorney, Agent, or Firm—Wenderoth, Lind & Ponack

[57] ABSTRACT

An analyzer compensation circuit for compensating for the fluctuations in the intensity of the light source or for stains on the windows of cells in an analyzer. A pair of D-A converters are respectively connected to compensating and measuring light detectors. An up/down counter is arranged to count either up or down in response to the output of a comparator. The comparator compares the output of the D-A converter connected to the compensating detector with a reference value and the output of the up/down counter is connected to both of the D-A converters such that the output of the converter connected to the compensating detector is adjusted to be equal to the reference value. Since the other D-A converter is also connected to the output of the up/down counter, the output of the other D-A converter has been compensated for fluctuations in the light intensity or stains on the windows on cells used in the analyzer.

2 Claims, 3 Drawing Figures

ANALYZER COMPENSATION CIRCUIT

BACKGROUND OF THE INVENTION

1. Field of the Invention

The present invention relates to a compensation circuit for compensating for the fluctuations in the intensity of the light source or for stains on the windows of cells in an analyzer.

2. Description of the Prior Art

A circuit as shown in FIG. 1 or FIG. 2 has been used as a circuit for compensating for the fluctuations in the intensity of a light source. FIG. 1 shows a circuit in which a compensating resistance VR can be adjusted by an AGC circuit (Automatic Gain Control circuit) while light passing through an object to be measured 2 from a light source 1 is detected by a detector 3. The resulting detector output signal is amplified by an amplifier 4 after passing through the compensating resistance VR and output as signal $e_o$. According to this circuit, it is necessary to carry out an operation to adjust the resistance VR by means of the AGC circuit 5 by switching ON (i.e.—closing) a switch SW so that the output signal $e_o$ may be made equal to a standard reference voltage $E_s$, the resistance VR being adjusted after removing the object 2 to be measured in order to compensate for the fluctuations in the intensity of the light source 1. Accordingly, it is impossible to carry out measurements on the object 2 during this adjustment operation. That is to say, this circuit has a disadvantage in that the measurements can only be carried out intermittently and fast fluctuations in the intensity of the light source cannot be sufficiently compensated for.

On the other hand, FIG. 2 shows a circuit in which a measured signal detected by a detector 3 is fed to a logarithmic amplifier 6; a monitor signal from a light source 1 is detected by a detector 3' whose output is fed to a logarithmic amplifier 7; the difference between the output signals of amplifiers 6 and 7 is determined by means of a differential amplifier 8, and the fluctuation in the intensity of the light source can be compensated for. According to this circuit, although continuous measurements are possible because the compensating operations can be carried out during measurements, it has disadvantages in that the errors are increased with a decrease in the intensity of the light source and an adequate compensation for the fluctuations in the intensity of the light source is thereby impossible; in addition, the dynamic range (i.e.—the ratio of the maximum value of the signal level which can be treated by an amplifier divided by the minimum value of the signal level thereof) is decreased because of the fact that the division of analog quantities is carried out.

Although the above-noted description relates to the compensation for the fluctuations in the intensity of a light source, a similar compensating method as that described above is used with the same disadvantages as that described above in order to compensate for stains on the windows of cells.

SUMMARY OF THE INVENTION

It is an object of the present invention to provide a compensation circuit which can correctly compensate for the fluctuations in the intensity of a light source and stains on the windows of cells without increasing errors in spite of decreases in the intensity of the light source and heavy stains on the windows of cells.

DESCRIPTION OF THE PREFERRED EMBODIMENT

Figure 1:
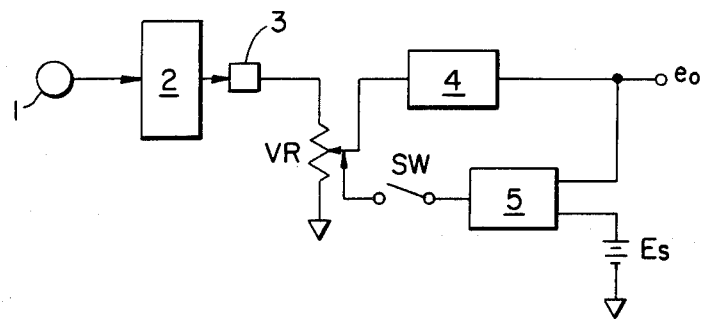
FIGS. 1 and 2 show conventional compensation circuits.
Figure 2:
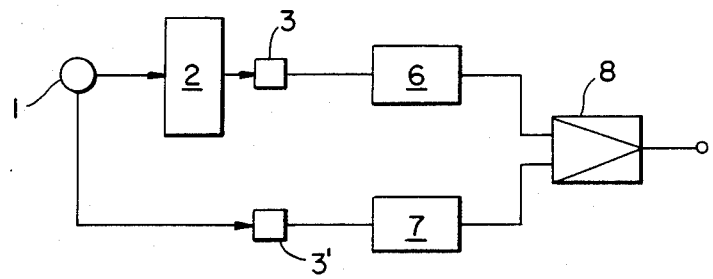
Figure 3:
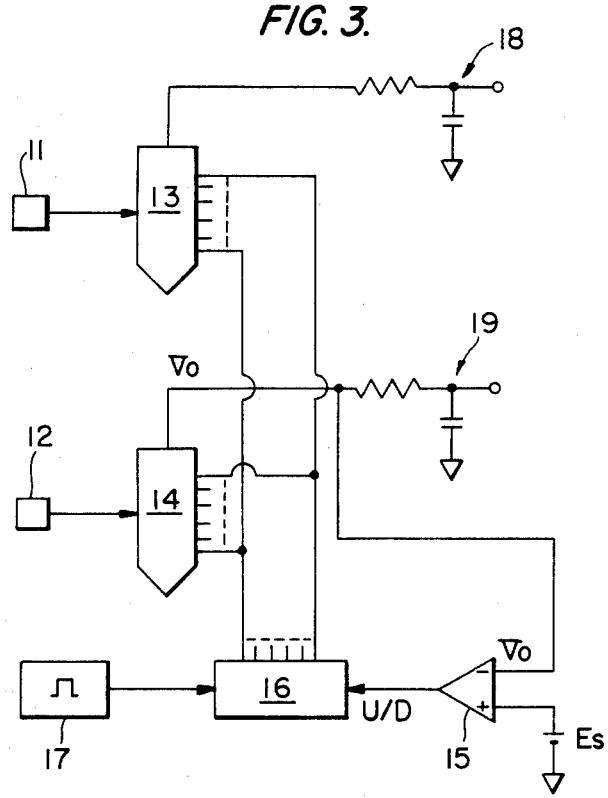
FIG. 3 shows one preferred embodiment of a compensation circuit according to the present invention.

One of the preferred embodiments of a compensation circuit according to the present invention will be described below by reference to FIG. 3. A measuring detector 11 and a compensating detector 12 is shown. A light passing through an object to be measured is arranged to be incident to the measuring detector 11 and a monitor light is arranged to be incident to the compensating detector 12. The monitor light comes from a light source (not shown) in the case of compensating for the fluctuations in the intensity of a light source while two lights having different wavelengths are arranged to pass separately through a cell so as to be incident to the detector 11 and the detector 12 in the case of compensating for stains on the windows of a cell. A D-A converter 13 of the multiplying type is fed a detected signal from the measuring detector 11. A D-A converter 14 of the multiplying type is fed a detected signal from the compensating detector 12. A comparator 15 compares an output voltage $V_o$ from the D-A converter 14 with the standard voltage $E_s$. An up/down counter 16 is switched so as to either count up or count down in dependence upon the comparison output of the comparator 15. The up/down counter 16 is switched to count up when $E_s$ is larger than $V_o$ and the up/down counter 16 is switched to count down when $E_s$ is smaller than $V_o$. A clock pulse generator 17 provides clock pulses to the counter 16.

The counter 16 counts up or counts down clock pulses generated by the clock pulse generator 17 in dependence upon the output signals of the comparator 15. The count stored in the counter 16 is fed in parallel to the D-A converters 13 and 14. The stored bits of the converter 14 are automatically adjusted so that an output $V_o$ of the converter 14 on the compensating detector side may be equal to the standard voltage $E_s$ while stored bits of the converter 13 are automatically adjusted so as to be the same as the stored bits of the converter 14.

According to this construction, an output voltage $V_o$ from the converter 14 can follow the standard voltage $E_s$ even though the detected signals from the compensating detector 12 are changed due to the fluctuations in the intensity of the light source or stains on the windows of a cell. The converter 13 on the measuring detector side is simultaneously automatically adjusted in the same manner as the converter 14. Consequently, although detected signals from the measuring detector 11 are also changed due to the fluctuations in the intensity of the light source or stains on the windows of a cell, these detected signals are corrected by multiplying them by the bits stored in the converter 13 so as to obtain signal outputs from the converter 13 which are compensated for the fluctuations in the intensity of the light source and for stains on the windows of a cell.

Lowpass filters 18 and 19 have a cutoff frequency which is smaller than the frequency of the clock pulses. In addition, although only one detecting (measuring) detector 11 and only one converter 13 are used in the above-described preferred embodiment, a plurality of measuring detectors 11 and converters 13 may be used. In such a case, it is only necessary to connect the system so that the contents of up/down counter 16 is fed in parallel to the separate converters.

An analyzer compensation circuit according to the present invention has the following effects due to the above-described construction:

(a) The compensation for the fluctuations in the intensity of the light source and for stains on the windows of a cell can be carried out even during the continuous measurements of an object because the measurements are carried out by means of a measuring detector and a D-A converter of the multiplying type to which the detected signals from the measuring detector are fed and an automatic adjustment of the bits of the D-A converter of the multiplying type is carried out by means of a circuit consisting of a compensating detector, another D-A converter, a comparator and an up/down counter.

(b) The decrease in the intensity of the light source and heavy stains on the windows of a cell do not lead to an increase in errors and the like and a highly accurate compensation is thereby always possible because the bits of the D-A converter of the multiplying type from the compensating detector side, to which the detected signals of a compensating detector are fed, are automatically adjusted so that an output voltage from the D-A converter of the multiplying type may be equal to a standard voltage and simultaneously, the bits of a D-A converter of the multiplying type from the measuring detector side are automatically adjusted to be the same as the bits D-A converter of the multiplying type from the compensating detector side without adopting the method in which the light to be measured is conventionally divided by a monitor light in spite of a circuit which can compensate during object measurements.

I claim:

1. An analyzer output compensation circuit comprising:

a compensating detector for converting a light incident thereon into an electrical signal output;

a measuring detector for converting a light incident thereon into an electrical output signal;

first and second D-A converters of the multiplying type, said first converter connected to said measuring detector, and said second converter connected to said compensating detector;

an up/down counter having its digital outputs operatively connected in parallel to said first and second converters;

a clock pulse generator means for providing clock pulses to said up/down counter;

a reference voltage;

a voltage comparator having its output operatively connected to said up/down counter's control input, said comparator's inputs respectively connected to said reference voltage and to an output of said second converter;

wherein said first converter output corresponds to the multiplication of the count stored in said up/down counter multiplied by the output of said measuring detector and the output of said second converter corresponds to the count stored in said up/down counter multiplied by the output of said compensating detector;

and wherein said up/down counter is controlled by said comparator to count either up or down to enable said output of said second converter to be equal to said reference voltage and simultaneously the first converter receives the same count stored in said up/down counter, and said measuring detector output is available as a compensated analyzer output, whereby fluctuations of the intensity of said lights is compensated for.

2. An analyzer output compensation circuit as claimed in claim 1, in which a plurality of measuring detectors and a plurality of convertors connected to said measuring detectors are used and the system is connected so that the contents of said up/down counter is fed in parallel to the separate convertors.

* * * * *